US010918654B1

(12) United States Patent
Kida et al.

(10) Patent No.: US 10,918,654 B1
(45) Date of Patent: *Feb. 16, 2021

(54) RUTIN COMPOSITIONS

(71) Applicant: Alps Pharmaceutical Ind. Co., Ltd., Gifu (JP)

(72) Inventors: Hiroaki Kida, Gifu (JP); Naoto Yamaguchi, Gifu (JP); Mitsunori Ono, Nagano (JP)

(73) Assignee: ALPS Pharmaceutical Ind. Co., Ltd., Gifu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/790,330

(22) Filed: Feb. 13, 2020

Related U.S. Application Data

(60) Provisional application No. 62/904,169, filed on Sep. 23, 2019.

(51) Int. Cl.
| | | |
|---|---|---|
| A61K 31/7048 | (2006.01) | |
| A61K 31/195 | (2006.01) | |
| A61K 31/375 | (2006.01) | |
| A61K 31/714 | (2006.01) | |
| A61K 31/506 | (2006.01) | |
| A61K 31/455 | (2006.01) | |
| A61K 31/675 | (2006.01) | |
| A61K 9/00 | (2006.01) | |
| A61K 9/08 | (2006.01) | |
| A61K 9/06 | (2006.01) | |

(52) U.S. Cl.
CPC ........ *A61K 31/7048* (2013.01); *A61K 9/0053* (2013.01); *A61K 9/06* (2013.01); *A61K 9/08* (2013.01); *A61K 31/195* (2013.01); *A61K 31/375* (2013.01); *A61K 31/455* (2013.01); *A61K 31/506* (2013.01); *A61K 31/675* (2013.01); *A61K 31/714* (2013.01)

(58) Field of Classification Search
None
See application file for complete search history.

(56) References Cited

U.S. PATENT DOCUMENTS

| | | | |
|---|---|---|---|
| 2,451,772 A | 10/1948 | Plungian | |
| 2,646,428 A | 7/1953 | Chabrier | |
| 2,975,168 A | 3/1961 | Favre et al. | |
| 4,285,964 A | 8/1981 | Niebes et al. | |
| 6,491,948 B1 | 12/2002 | Buchholz et al. | |
| 8,426,459 B2 | 4/2013 | Stuchlik et al. | |
| 2006/0099239 A1* | 5/2006 | Coleman | A61K 31/353 424/440 |
| 2009/0082400 A1 | 3/2009 | Lee et al. | |
| 2009/0149481 A1* | 6/2009 | Azuma | A23L 33/15 514/263.31 |
| 2009/0325906 A1 | 12/2009 | Robbins et al. | |
| 2010/0113373 A1 | 5/2010 | Phillips et al. | |
| 2010/0204204 A1 | 8/2010 | Zaworotko et al. | |
| 2012/0083460 A1 | 4/2012 | Emura et al. | |
| 2019/0060272 A1 | 2/2019 | Aleksandrovich et al. | |

FOREIGN PATENT DOCUMENTS

| | | |
|---|---|---|
| CN | 101301477 A | 11/2008 |
| DE | 2020/08006741 U1 | 10/2009 |
| EP | 0075626 A1 | 4/1983 |
| EP | 1669462 A1 | 6/2006 |
| GB | 2198041 A | 6/1988 |
| JP | S59232054 A | 12/1984 |
| JP | 6176552 A | 4/1986 |
| JP | H0654664 A | 3/1994 |
| JP | 2003/171274 A | 6/2003 |
| JP | 2005/198642 A | 7/2005 |
| JP | 2007325588 A | 12/2007 |
| JP | 2008092869 A | 4/2008 |
| JP | 2010/126503 A | 6/2010 |
| JP | 2010/248148 A | 11/2010 |
| JP | 2926411 B2 | 7/2011 |
| JP | 2015/181399 A | 10/2015 |
| JP | 2015208241 A | 11/2015 |
| JP | 2017/131215 A | 8/2017 |
| JP | 2019/024500 A | 2/2019 |
| RU | 2545905 C1 | 4/2015 |
| WO | WO-0012085 A1 | 3/2000 |
| WO | WO-2005030975 A1 | 4/2005 |
| WO | WO-2007114304 A1 | 10/2007 |
| WO | WO-2010/029913 A1 | 3/2010 |
| WO | WO-2011104667 A1 | 9/2011 |
| WO | WO2010110328 A1 | 10/2012 |
| WO | WO-2019208574 A1 * | 10/2019 ............. A61K 8/602 |
| WO | WO-2019/230013 A1 | 12/2019 |

OTHER PUBLICATIONS

Hamad, I., AbdElgawad, H., Al Jaouni, S., Zinta, G., Asard, H., Hassan, S., . . . & Selim, S. (2015). Metabolic analysis of various date palm fruit (*Phoenix dactylifera* L.) cultivars from Saudi Arabia to assess their nutritional quality. Molecules, 20(8), 13620-13641. (Year: 2015).*

Acquaviva et al "Beneficial Effects of Rutin and L-Arginine Coadministration in a Rat Model of Liver Ischemia-Reperfusion Injury" American Journal of Physiology-Gastrointestinal and Liver Physiology vol. 296, pp. 664-670, 2009.

Akiyama et al "Constituents of Enzymatically Modified Isoquercitrin and Enzymatically Modified Rutin (Extract)" Journal of the Food Hygienic Society of Japan vol. 41, pp. 54-60, 2000.

çelik et al "Antioxidant Capacity of Quercetin and its Glycosides in the Presence of β-Cyclodextrins: Influence of Glycosylation on Inclusion Complexation" Journal of Inclusion Phenomena and Macrocyclic Chemistry vol. 83, pp. 309-319, 2015.

Morling et al "Rutosides for Prevention of Post-Thrombotic Sydrome (Review)" Cochrane Database of Systematic Reviews vol. 11, pp. 1-17, 2018.

(Continued)

*Primary Examiner* — Dale R Miller
(74) *Attorney, Agent, or Firm* — Cesari and McKenna, LLP

(57) ABSTRACT

A water-soluble composition containing rutin, L-arginine, and an alkali salt of ascorbic acid in which the molar ratio between the rutin, L-arginine, and the alkali salt of ascorbic acid is 1:1.6-3.0:0.1-2.0.

16 Claims, 3 Drawing Sheets

(56) References Cited

OTHER PUBLICATIONS

Morling et al "Rutosides for Treatment of Post-Thrombotic Syndrome (Review)" Cochrane Database of Systematic Reviews vol. 4, pp. 1-26, 2013.

Punithavathi et al "Protective Effects of Rutin on Mitochondrial Damage in Isoproterenol-Induced Cardiotoxic Rats: An in Vivo and in Vitro Study" Cardiovascular Toxicology vol. 10, pp. 181-189, 2010.

Abdelkader et al "Investigation into the Emerging Role of the Basic Amino Acid L-Lysine in Enhancing Solubility and Permeability of BCS Class II and BCS Class IV Drugs" Pharm Res vol. 35, pp. 1-18, 2018.

Hollman "Determinants of the Absorption of the Dietary Flavonoid Quercetin in Man" State Institute for Quality Control of Agricultural Products. 1997.

Vrijsen et al "Antiviral Activity of Flavones and Potentiation by Ascorbate" Journal of General Virology vol. 69, pp. 1749-1751, 1988.

Yamasaki et al "Flavonoid-Peroxidase Reaction as a Detoxification Mechanism of Plant Cells Against $H_2O_2$" Plant Physiology vol. 115, pp. 1405-1412, 1997.

* cited by examiner

RUTIN COMPOSITIONS

CROSS-REFERENCE TO RELATED APPLICATIONS

This application claims the benefit of U.S. Provisional Application No. 62/904,169, filed on Sep. 23, 2019. The content of the prior application is hereby incorporated by reference in its entirety.

BACKGROUND

Rutin, an O-glycosyl flavonoid, exhibits a broad spectrum of biological activities.

For example, it has been shown to prevent the formation of blood clots. Preventing blood clots can help lower the chances of developing life-threatening conditions such as myocardial infarction, stroke, pulmonary embolism, and deep vein thrombosis. See Punithavathi et al., Cardiovasc. Toxicol., 2010, 10(3):181-189, Ortolani et al., Transplant Proc., 1995, 27(5):2877-2888), Morling et al. 2013, Cochrane Database Syst. Rev. 4:April 30, and Morling et al., 2018, Cochrane Database Syst Rev. 11:November 8.

In another example, rutin has been tested for treating chronic venous insufficiency (CVI) CVI is a common condition caused by valvular dysfunction with or without associated obstruction, usually in the lower limbs.

However, rutin has low bioavailability due to poor absorption that limits its potential as a therapeutic agent. Enzymatically modified rutin (EMR) with higher water solubility has been developed to improve the bioavailability of rutin. See Toyo Sugar Refining Co., Ltd HP (alfa G-rutin). Yet, EMR is a mixture of at least three bioactive rutin derivatives. See Akiyama et al., J. Food Hyg. Soc. Japan, 1999, 41:54-60. It is impractical to use such a mixture of active ingredients as a drug in humans according to present US Federal Drug Administration guidelines.

There is a need to develop compositions demonstrating high oral absorption of rutin with improved water solubility without the above-described drawbacks.

SUMMARY

To address the above need, a water-soluble composition is provided that contains rutin, L-arginine, and an alkali salt of ascorbic acid. In the composition, the molar ratio between the rutin, L-arginine, and the alkali salt of ascorbic acid is 1:1.6-3.0:0.1-2.0.

The details of the invention are set forth in the description below. Other features, objects, and advantages of the invention will be apparent from the detailed description, the drawings, and from the appended claims.

BRIEF DESCRIPTION OF THE DRAWINGS

The description below refers to the accompanying drawings, of which.

DETAILED DESCRIPTION

Figure 1:
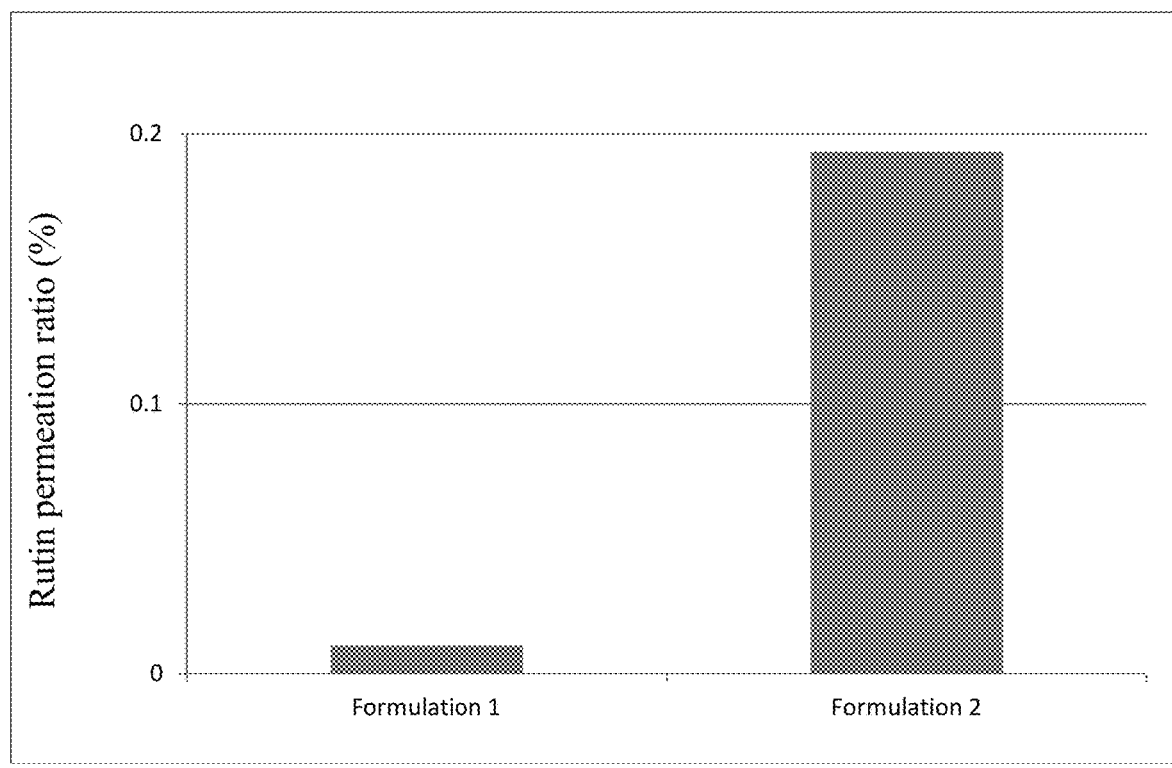
FIG. 1 is a bar graph showing permeation ratios (%) of formulation 1 (Rutin) and formulation 2 (Rutin/Arg) into Caco-2 cells.

As mentioned above, a water-soluble composition is disclosed that contains L-arginine, rutin, and an ascorbic acid alkali salt. The molar ratio between these three components is 1:1.6-3.0:0.1-2.0. In another composition of the invention the ratio is 1:1.8-2.8:0.2-1.5. An exemplary water-soluble composition contains rutin, L-arginine, and an alkali salt of ascorbic acid at a molar ratio of 1:2.3:0.42.

Notably, the alkali salt of ascorbic acid can be a sodium salt or a potassium salt. In a particular composition, the alkali salt is a sodium salt.

The water-soluble pharmaceutical composition can also include vitamin B1, vitamin B3, vitamin B6, vitamin B9, or vitamin B12, in addition to rutin, L-arginine, and an alkali salt of ascorbic acid. The molar ratio of rutin to each water soluble vitamin in the composition can be 1:0.01-0.1.

The water-soluble compositions of rutin, L-arginine, and alkali salt of ascorbic acid described above can be produced by the methods set forth in US Patent Application Nos. 62/661,255 and 62/720,651, and International Application No. PCT/JP2019/017262, the contents of which are incorporated herein in their entireties.

In the water-soluble composition, rutin can be present in a content of 10 wt % or higher (e.g., 20 wt % or higher, 30 wt % or higher, and 50 wt % or higher). L-arginine is also present at 10 wt % or higher (e.g., 20 wt % or higher, 30 wt % or higher, and 50 wt % or higher). The alkali salt of ascorbic acid is present at 2 wt % or higher (e.g., 4 wt % or higher, 6 wt % or higher, and 10 wt % or higher).

The water-soluble composition, either in solid form or aqueous form, can be incorporated into formulations for pharmaceutical, medical, food preservation, or cosmetic use.

For example, the water-soluble composition can be formulated for oral administration as a liquid, a capsule, a tablet, a pill, or a gel. The composition in capsule or tablet form can have an enteric coating.

The formulations for oral administration can also contain a pharmaceutically active agent, a pharmaceutically acceptable excipient, or a combination thereof. These formulations can be a pharmaceutical, a dietary supplement, a natural health product, a cosmetic product, a food product, or a beverage.

If formulated for topical administration, the composition can be a solution, a liniment, a lotion, a cream, an ointment, a paste, a gel, or an emulgel. Topical formulations can also contain a pharmaceutically active agent, a topically acceptable excipient, or a combination thereof. Such formulations can be a cosmetic product, a skin care product, or a pharmaceutical.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference in their entirety.

Example 1: Preparation of an Aqueous Rutin/L-Arginine/Ascorbic Acid Composition

A composition containing rutin, L-arginine, and ascorbate was prepared in water by mixing 0.0071 mol rutin with an aqueous solution containing 0.020 mol L-arginine, heating the mixture to 80° C. until the rutin dissolved completely, and adding 0.0010 mol sodium ascorbate.

After cooling the above solution, the stability of rutin was tested by heating the mixture to 50° C. and quantifying the amount of intact rutin remaining by HPLC after 0 h, 5 h, and 24 h. The results showed that the amount of intact rutin at 5 h and 24 h at 50° C. was 100% and 97.2%, respectively, of the initial amount of rutin in the solution.

A similar study was performed to assess the stability of a flavonoid related to rutin, i.e., catechin, after dissolving it with L-arginine and sodium ascorbate. The amount of intact catechin remaining in the solution after 5 h and 24 h at 50° C. was 30.8% and 2.3%, respectively. It was quite unexpected that only 2.8% of the rutin degraded after 24 h, as compared to 97.7% of the catechin under identical conditions.

Example 2: Preparation of a Solid Rutin/L-Arginine/Ascorbic Acid Composition

A second rutin/L-arginine/ascorbate composition was prepared by dissolving 125.0 g of L-arginine (0.72 mol) in 650 ml water heated to 45° C., adding 22.9 g of L-ascorbic acid sodium salt (0.12 mol) and 29.9 g of hydrogenated dextrin and stirring until fully dissolved. To the solution, 170.3 g of rutin trihydrate (0.26 mol) was added and the resulting mixture heated at 80° C. for 30 min. Upon complete dissolution of the rutin, the solution was spray dried and sieved at 80 mesh to provide a yellow orange solid composition (326.9 g).

Example 3: Preparation of Rutin Pharmaceutical Formulations

Formulations of rutin/ascorbate and rutin/L-arginine/ascorbate were prepared with the components shown in Table 1 below. For dissolution studies, the formulations were used as is. For clinical studies, the formulations were encapsulated in size #1 acid resistant delayed release hypromellose capsules (DRcaps™) manufactured by Capsugel.

TABLE 1

Rutin formulation components

| Ingredient | Formulation 1 | Formulation 2 |
|---|---|---|
| rutin (mg)/(w/w %) | 250 mg/56.7% | 250 mg/42.4% |
| L-arginine (%) | — | 31.0% |
| ascorbic acid Na salt (w/w %) | 7.7% | 5.8% |
| dextrin (w/w %) | 29.7% | 16.4% |
| glycerin fatty acid ester (w/w %) | 5.9% | 4.4% |
| Total (w/w %) | 100% | 100% |

Example 4: Solubility Test

The ability of rutin to dissolve in water from Formulation 1 and Formulation 2 was tested as set forth, infra.

An amount of Formulation 1 containing 250 mg of rutin and an amount of Formulation 2 containing 250 mg of rutin were each added to separate 25 mL of distilled $H_2O$ and agitated for 30 s. After an aliquot was removed (0 min.), each mixture was heated at 37° C. with slow agitation. Aliquots were collected from each mixture at 5 min. and 30 min. after heat treatment began. Each aliquot was passed through a 0.45 μm filter and the rutin concentration in the filtrate measured by HPLC. The results are shown below in Table 2.

TABLE 2

Water solubility of rutin

| Incubation time | Formulation 1 | Formulation 2 | Fold difference |
|---|---|---|---|
| 0 min. | 0.036 mg/ml | 8.4 mg/ml | 210 |
| 5 min. | 0.064 mg/ml | 9.6 mg/ml | 160 |
| 30 min. | 0.073 mg/ml | 9.8 mg/ml | 140 |

The results showed that the amount of rutin dissolving from Formulation 2, i.e., rutin/L-arginine/ascorbate, was 140 to 210-fold greater than the amount of rutin dissolving from Formulation I, which is free of L-arginine. Clearly, Formulation 2 contains significantly more soluble rutin, as compared to Formulation 1.

Example 4 Permeation Study in Caco-2 Cells

Permeation of a drug into cultured intestinal Caco-2 cells is measured to predict the relative absorption rate of the drug when given orally.

The formulations described above in Example 3 were dissolved separately into a solution. A 500 μL aliquot of each solution was added to the apical side of Caco-2 cells that had been cultured for 19 days, and 2,000 μL of HBSS buffer was placed on the basolateral side of the cells. The cells were cultured in an incubator for 2 hours at 37° C., after which media was recovered from both the apical and basolateral sides of the cells. The concentration of rutin in the media was determined by HPLC, and the degree of absorption from the apical side to the basolateral side was determined by the following equation:

Permeation rate (%)=Permeation amount of basolateral side (nM)/Loaded amount of apical side (nM)×100

The results are shown in FIG. 1. Formulation 2, which contained rutin, L-arginine, and ascorbate exhibited a remarkable 18-fold increase in permeation (absorption) rate, as compared to Formulation 1, which contained rutin and ascorbate but lacked L-arginine.

Example 5: Clinical Pharmacokinetic Study

A randomized clinical pharmacokinetic study was performed to compare the two different rutin formulations described above in Example 2 administered in a single dose to 8 volunteers under fasting conditions. Healthy males between the ages of 25 and 39 years inclusive having body mass index values within the range of 18.6-24.7 participated in the study.

Capsules containing formulations 1 and 2 shown in Table 1 were prepared as described above. Each volunteer took (i) four capsules containing formulation 1 (rutin/ascorbate; 1000 mg rutin total), (ii) two capsules containing formulation 2 (rutin/L-arginine/ascorbate; 500 mg rutin total), or (iii) four capsules of formulation 2 (rutin/L-arginine/ascorbate; 1000 mg rutin) on three test days, administered according to a previously randomized sequence.

Rutin levels were measured in blood samples removed from the participants before dosing (0 h) and 0.5 h, 1 h, 2 h, 4 h, and 8 h after dosing following established procedures, with certain samples removed 48 h after dosing. More specifically, in order to measure rutin levels, plasma prepared from each blood sample was treated first to deconjugate rutin and its metabolites into aglycones quercetin and isorhamnetin, which were subsequently quantified by HPLC.

Briefly, 200 μl plasma samples were mixed with 10 μl 10% dithiothreitol and 50 μl 0.58 mol/L acetic acid. The mixture was treated with 100 U of beta-glucuronidase type H-5 (which possesses beta-glucuronidase and sulfatase, i.e., deconjugation, activity) in 0.1 M sodium acetate buffer (pH5.0) for 120 min at 37° C.

After deconjugation, 500 μl of 10 mM oxalic acid was added to each sample and the mixture centrifuged at 10,000×g for 5 min. All treated samples were subjected to solid phase extraction using preconditioned Oasis HLB cartridges as directed by the manufacturer (Waters, Milford Mass. USA). The extracted eluates were evaporated under nitrogen, reconstituted in methanol, and subjected to HPLC analysis by loading each eluate on a C18 column (Waters ACQUITY UPLC BEH; 1.7 μm, 2.1×100 mm), applying a gradient solvent system of 0.1% formic acid in $H_2O$/0.1% formic acid in acetonitrile HPLC, and detecting the presence of quercetin and isorhamnetin with an ACQUITY UPLC I-class Plus•Xevo TQ-S micro (Waters). The concentration of each aglycone was calculated using a standard curve prepared with authentic quercetin and isorhamnetin internal standards. The analytical limit for quercetin and isorhamnetin under the above conditions was 3.3 nM.

Figure 2:
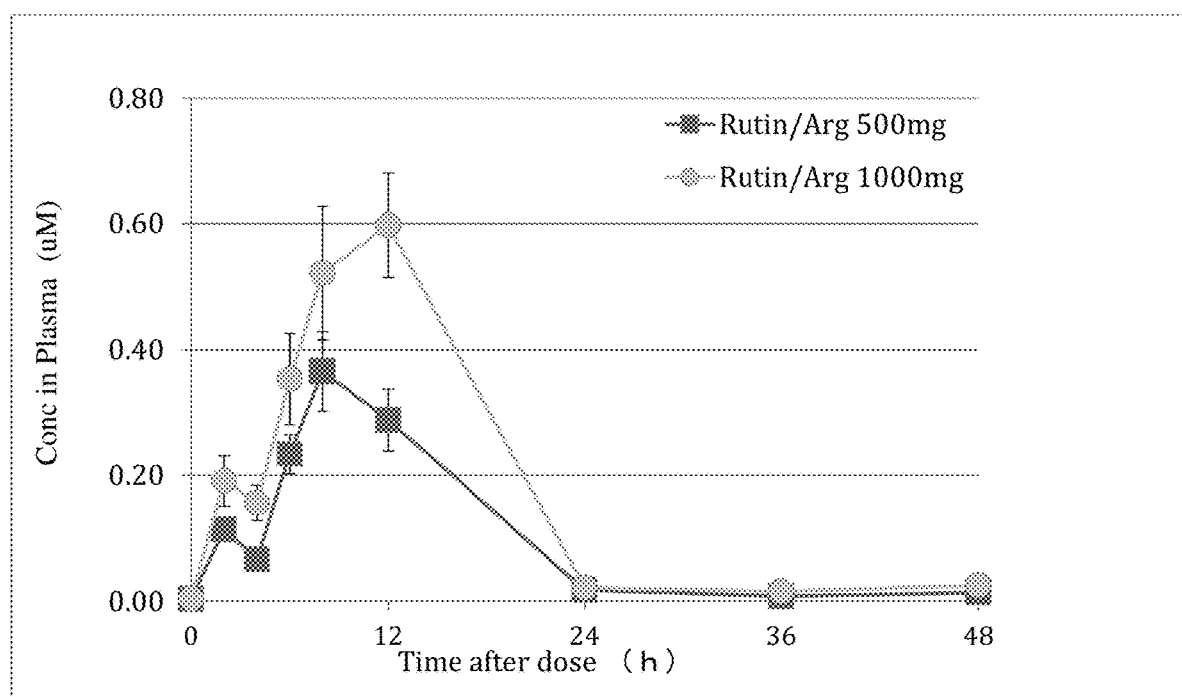
FIG. 2 is a plot of rutin concentration in plasma versus time.
Figure 3:
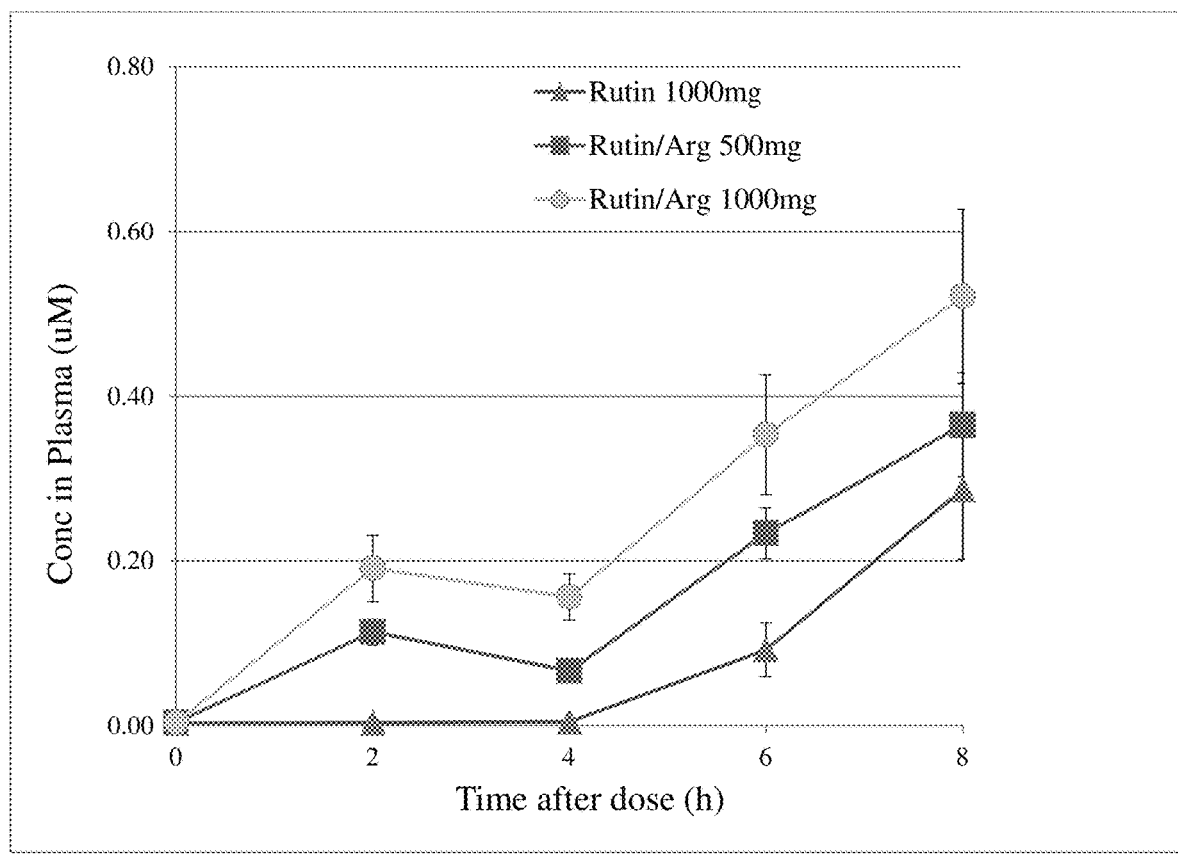
FIG. 3 is a plot of rutin concentration in plasma versus time.

The results are shown in FIGS. 2 and 3.

FIG. 2 shows the time course of plasma concentrations of conjugated rutin metabolites during the 48 h period after consuming 500 mg of rutin as rutin/L-arginine/ascorbate and after consuming 1000 mg rutin also as rutin/L-arginine/ascorbate. The plasma concentration of the metabolites increased steadily, reaching a maximum level at 8.5 h (500 mg) and 9.3 h (1000 mg) after intake. Levels decreased thereafter to background after 24 h.

Pharmacokinetic values calculated from profiles similar to those depicted in FIG. 2 are shown in Table 3 below.

TABLE 3

Pharmacokinetics of rutin compositions

| Parameters | Treatment | |
|---|---|---|
| | rutin/L-arg/ ascorbate 500 mg | rutin/L-Arg/ ascorbate 1000 mg |
| AUC (μmol · h/L) (0-8 h) | 1.20 ± 0.21 | 1.93 ± 0.35 |
| $C_{max}$ (μM) | 0.41 ± 0.06 | 0.65 ± 0.08 |
| $T_{max}$ (h) | 8.5 ± 0.7 | 9.3 ± 0.8 |
| AUC (μmol · h/L) (0-∞ h) | 4.60 ± 0.50 | 8.35 ± 1.14 |

FIG. 3 shows the time course of plasma concentrations of conjugated rutin metabolites during the 8 h period after dosing with 500 mg of rutin as rutin/ascorbate, 500 mg of rutin as rutin/L-arginine/ascorbate, and 1000 mg rutin also as rutin/L-arginine/ascorbate. The pharmacokinetic profile at 8 h of both rutin/L-arginine/ascorbate 500 mg and 1000 mg showed appearance of rutin metabolites in plasma much faster than those of rutin without L-Arginine.

Pharmacokinetic values calculated from profiles similar to those depicted in FIG. 3 are shown in Table 4 below.

TABLE 4

Comparative pharmacokinetics of rutin and rutin compositions

| Parameters | Treatment | | |
|---|---|---|---|
| | rutin 1000 mg | rutin/ L-arginine/ascorbate 500 mg | rutin/ L-arginine/ascorbate 1000 mg |
| AUC (μmol · hr/L) (0-8 h) | 0.49 ± 0.15 | 1.20 ± 0.21 | 1.93 ± 0.35 |
| $C_{max}$ (μM) | 0.29 ± 0.09 | 0.37 ± 0.06 | 0.53 ± 0.11 |
| $T_{max}$ (hr) | 8.0 ± 0 | 7.5 ± 0.3 | 7.5 ± 0.3 |

The calculated area under the curve (AUC) of rutin/L-arginine/ascorbate 500 mg and 1000 mg showed a dose-dependent relationship. Further, the AUCs of rutin/L-arginine/ascorbate 500 mg and 1000 mg from 0-8 h were about 2.5 and 4.0 times higher than that of rutin without L-arginine, respectively. Clearly, the oral absorption of rutin was greatly improved by combining it with L-arginine and ascorbate.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A water-soluble composition comprising rutin, L-arginine, and an alkali salt of ascorbic acid, wherein a molar ratio between the rutin, L-arginine, and the alkali salt of ascorbic acid is 1:1.6-3.0:0.1-0.46.

2. The water-soluble composition of claim 1, wherein the alkali salt of ascorbic acid is a sodium salt or a potassium salt.

3. The water-soluble composition of claim 2, wherein the composition is an oral formulation selected from the group consisting of a liquid, a capsule, a tablet, a pill, and a gel.

4. The water-soluble composition of claim 2, wherein the composition is a topical formulation selected from the group consisting of a solution, a liniment, a lotion, a cream, an ointment, a paste, a gel, and an emulgel.

5. The water-soluble composition of claim 1, further comprising vitamin B1, vitamin B3, vitamin B6, vitamin B9, or vitamin B12.

6. The water-soluble composition of claim 5, wherein the composition is an oral formulation selected from the group consisting of a liquid, a capsule, a tablet, a pill, and a gel.

7. The water-soluble composition of claim 5, wherein the composition is a topical formulation selected from the group consisting of a solution, a liniment, a lotion, a cream, an ointment, a paste, a gel, and an emulgel.

8. The water-soluble composition of claim 2, further comprising vitamin B1, vitamin B3, vitamin B6, vitamin B9, or vitamin B12.

9. The water-soluble composition of claim 2, wherein the molar ratio between the rutin, L-arginine, and the alkali salt of ascorbic acid is 1:1.8-2.8:0.2-0.46.

10. The water-soluble composition of claim 9, wherein the molar ratio between the rutin, L-arginine, and the alkali salt of ascorbic acid is 1:2.3:0.42.

11. The water-soluble composition of claim 9, wherein the alkali salt of ascorbic acid is a sodium salt or a potassium salt.

12. The water-soluble composition of claim 9, wherein the composition is an oral formulation selected from the group consisting of a liquid, a capsule, a tablet, a pill, and a gel.

13. The water-soluble composition of claim 9, wherein the composition is a topical formulation selected from the group consisting of a solution, a liniment, a lotion, a cream, an ointment, a paste, a gel, and an emulgel.

14. The water-soluble composition of claim 9, further comprising vitamin B1, vitamin B3, vitamin B6, vitamin B9, or vitamin B12.

15. The water-soluble composition of claim 14, wherein the composition is an oral formulation selected from the group consisting of a liquid, a capsule, a tablet, a pill, and a gel.

16. The water-soluble composition of claim 14, wherein the composition is a topical formulation selected from the group consisting of a solution, a liniment, a lotion, a cream, an ointment, a paste, a gel, and an emulgel.

\* \* \* \* \*